United States Patent [19]
Moelling

[11] Patent Number: 5,849,900
[45] Date of Patent: Dec. 15, 1998

[54] INHIBITION OF VIRUSES BY ANTISENSE OLIGOMERS CAPABLE OF BINDING TO POLYPURINE RICH TRACT OF SINGLE-STRANDED RNA OR RNA-DNA HYBRIDS

[75] Inventor: Karin Moelling, Berlin, Germany

[73] Assignee: Max-Planck-Gesellschaft zur Forderung der Wissenschafter e.v., Gottingen, Germany

[21] Appl. No.: 412,376

[22] Filed: Mar. 28, 1995

Related U.S. Application Data

[63] Continuation-in-part of Ser. No. 954,184, which is a continuation of PCT/US93/09300 Sep. 29, 1993, abandoned.

[51] Int. Cl.$^6$ .................................................. C07H 21/04
[52] U.S. Cl. ............................................................. 536/24.5
[58] Field of Search .............................. 514/44; 536/24.5

[56] References Cited

U.S. PATENT DOCUMENTS

| | | | |
|---|---|---|---|
| 3,625,214 | 12/1971 | Higuchi .................................... | 128/260 |
| 4,789,734 | 12/1988 | Pierschbacher ......................... | 530/395 |
| 4,906,474 | 3/1990 | Langer et al. .......................... | 424/428 |
| 4,925,673 | 5/1990 | Steiner et al. ........................... | 424/455 |
| 5,138,045 | 8/1992 | Cook et al. .............................. | 536/27 |

FOREIGN PATENT DOCUMENTS

| | | | |
|---|---|---|---|
| 375408 | 6/1990 | European Pat. Off. .............. | 536/24.5 |
| WO 93/03141 | 2/1993 | WIPO . | |

OTHER PUBLICATIONS

PCT International Search Report dated Nov. 28, 1997, 5 pages.
Goodchild J, "Enchancement of ribozyme catalytic activity by a contiguous oligodeoxynucleotide (facilitator) and by 2'–O–methylation," Nucleic Acids Research, 1992, 20(17), 4607–4612.
Koizumi M. et al., "Cleavage of specific sites of RNA by designed ribozymes," Fed. of Euro. Biochem. Societies, 1988, 239(2), 285–288.
Pachuk c.j. et al., "Selective cleavage of bcr/abl chimeric RNAs by a ribozyme targeted to non–contiguous sequences," Nucleic Acids Research, 1994, 22(3), 301–307.
Tabler M. et al., "Catalytic antisense RNAs produced by incorporating ribozyme cassettes into cDNA," Gene, 1991, 108, 175–183.
Helene C. "The anti–gene strategy: Control of gene expression of triplex–forming–oligonucleotides." Anti–Cancer Drug Design 6: 569–584, 1991.
Volkmann S, et al. "Inhibition of HIV–1 reverse transcription of triplex–helix forming oligonucleotides with viral RNA." Nucl. Acids Res. 23: 1204–1212, 1995.
Jendis J, et al. "Inhibition of replication of fresh HIV type I patient isolates by a polypurine tract–specific self–complementary oligodeoxynucleotide." Aids Res. Human Retroviruses 12: 1161–1168, 1996.
Uhlmann E, et al. "Antisense oligonucleotides: A new therapeutic principle." Chemical Reviews 90 (4): 543–584, 1990.
Helene C. "The anti–gene strategy: Control of gene expression by triplex–forming–oligonucleotides." Anti–Cancer Drug Design 6: 569–584, 1991.
Stull RA, "Antigene, ribozyme and aptamer nucleic acid drugs: Progress and prospects." Pharmaceutical Research 12 (4); 465–483, 1995.
Gao X, et al. "A novel cationic liposome reagent for efficient transfection of mammalian cells." Biochem. and Biophys. Res. Commu. 179 (1): 280–285, Aug. 30, 1991.
Anfossi et al., "An Oligomer Complementary to c–myb–encoded mRNA Inhibits Proliferation of Human Myeloid Leukemia Cell Lines", PNAS USA 1989, 3379–3383.
Buck et al., "Phosphate–Methylated DNA Aimed at HIV–1 RNA Loops and Integrated DNA Inhibits Viral Infectivity", Science 1990, 248, 208–212.
Gait, M.J., ed., "Oligonucleotide Synthesis", IRL, Oxford, 1984.
Gregoriadis, G., "Liposomes", Chap. 14 in Drug Carriers in Biology and Medicine, Academic Press, 1979, pp. 287–341.
Hansen et al., "Identification and Characterization fo HIV–Specific RNase H by Monoclonal Antibody", The EMBO J.1988, 7, 239–243.
Hansen et al., "RNase H Activity Associated with Bacterially Expressed Reverse Transcriptase of Human T–cell Lymphotropic Virus III–Lymphadenopathy–associted Virus", J. Biol. Chem. 1987, 262, 12393–12396.
Hanvey, J.C. et al., "DNA Triple–Helix Formation at Physiologic pH and Temperature", Antisense Research and Development 1991, 1, 307–317.
Hayashi, T. et al., "RNA Packaging Signal of Human Immunodeficiency Virus Type 1", Virology 1992, 188, 590–599.
Huber, H.E. et al., "Processing of the Primer for Plus Strand DNA Synthesis by Human Immunodeficiency Virus 1 Reverse Transcriptase", J. of Biol. Chem. 1990, 265(18), 10565–10573.
Klysik, J. et al., "Parallel–Stranded DNA under Topological Stress: Rearrangement of $(dA)^{15}$–$(dT)^{15}$ to a $d(A–A–T)^n$ Triplex", Nucleic Acids Research 1991, 19(25), 7145–7154.
Loke, S.L. et al., "Delivery of cmyc Antisense Phosphorothioate Oligodeoxynucleotides to Hematopoietic Cells in Culture by Liposome Fusion: Specific Reduction in c–myc Protein Expression Correlates With Inhibition of Cell Growth and DNA Synthesis", Current Topics in Microbiology and Immunology 1988, 141, 282–289.

(List continued on next page.)

Primary Examiner—Douglas W. Robinson
Assistant Examiner—Amy J. Nelson
Attorney, Agent, or Firm—Woodcock Washburn Kurtz Mackiewicz & Norris, LLP

[57] ABSTRACT

The present invention provides methods of inhibiting a virus with which a vertebrate is infected and which replicates via an RNA template comprising the administration of an antisense or triplex-forming oligonucleotide or a derivative thereof capable of binding to a polypurine-rich tract in a region of single-stranded RNA or RNA-DNA hybrid, respectively. Chimeric oligonucleotides capable of forming triplex structures with single-stranded nucleic acids are also disclosed.

5 Claims, 3 Drawing Sheets

OTHER PUBLICATIONS

Maher et al., "Inhibition of DNA–Protein Interactions by Oligonucleotide–Directed DNA Triple Helix Formation: Progress and Prospects" in Prospects for Antisense Nucleic Therapy of Cancer and AIDS, Wickerstrom, Ed., Wiley–Liss 1991, 227–242.

Maher et al., "Kinetic Analysis of Oligodeoxyribonucleotide–directed Triplex–Helix Formation on DNA", *Biochemistry* 1990, 29, 8820–8826.

Maher III, L.J. et al., "Inhibition of DNA Binding Proteins by Oligonucleotide–Directed Triplex Helix Formation", *Science* 1989, 245, 725–730.

Mirabelli, C.K. et al., "In vitro and in vivo Pharmacologic Activities of Antisense Oligonucleotides", *Anti–Cancer Drug Design* 1991, 6, 647–661.

Moelling, K., "Minireview: The RNase H of HIV–1", *Med. Microbiol. Lett.* 1992, 1, 71–77.

Ono, A. et al,. "DNA Triplex Formation of Oligonucleotide Analogues Consisting of Linker Groups and Octamer Segments That Have Opposite Sugar–Phosphage Backbone Polarities",3 *Biochemistry* 1991, 30(14),9914–9921.

Postel, E.H. et al., "Evidence that a Triplex–Forming Oligodeoxyribonucleotide Binds tothe c–myc mRNA Levels", *PNAS USA* 1991, 88, 8227–8231.

Ratajczak et al., "In vivo Treatment of Human Leukemia in a scid Mouse Model with c–myb Antisense Oligodeoxynucleotides", *PNAS USA* 1992, 89, 11823–11827.

Rattray, A. and Champoux, "Plus–strand Priming by Moloney Murine Leukemia Virus. The Sequence Features Important for Cleavage by RNase H", *J. Mol. Biol.* 1989, 208, 445–456.

Sambrook, J. et al., "Molecular Cloning: A Laboratory Manual", Cold Spring Harbor Laboratory Press, Cold Spring, New York, 1989, pp. 9.50–9.51.

Shibahara et al., "Inhibition of Human Immunodeficiency Virus(HIV–1) Replication by Synthetic Oligo–RNA Derivatives", *Nucleic Acids Research* 1989, 17, 239–252.

Stein, C.A. et al., "Antisense Oligonucleotides as Therapeutic Agents–Is the Bullet Really Magical?" *Science* 1993, 261, 1004–1012.

Stein, C.A. and Cohen, "Oligodeoxynucleotides as Inhibitors of Gene Expression: A Review", *Cancer Research* 1988, 48, 2659–2668.

Sun et al., "Triple–Helix Formation by Oligodeoxynucleotides and α Oligodeoxynucleotide–Intercalator Conugates", *PNAS USA* 1991, 88, 6023–6027.

Tisdale, M. et al., "Mutations within the RNase H Domain of Human Immunodeficiency Virus Type 1 Reverse Transcriptase Abolish Virus Infectivity", *J. of Gen. Virol.* 1991, 72, 59–66.

Tseng, B.Y. et al., "Antisense Oligonucleotide Technology in the Development of Cancer Therapeutics", *Cancer Gene Therapy* 1994, 1(1), 65–71.

Uhlmann, E. et al., "Antisense Oligonucleotides: A New Therapeutic Principle", *Chemical Reviews* 1990, 90(4), 543–584.

Volkmann et al., "The Polypurine Tract, PPT, of HIV as Target for Antisense and Triplex–Helix–Forming Oligonucleoties", *Biochimie* 1993, 75, 71–78.

Weiss, R., "Upping the Antisense Ante", *Science News* 1991, 139, 108–109.

Westermann, P. et al., "Inhibition of Expresion of SV–40 Virus Large T–Antigen by Antisense Oligodeoxyribonucleotides", *Biomed. Biochim. Acta* 1989, 48, 85–93.

Wohrl, B. et al., "Mutations of a Conserved Residue Within HIV–1 Ribonuclease H Affect its Exo–and Endonuclease Activities", *J. Mol. Biol.* 1991, 220, 801–818.

Wohrl, B. and Moelling, "Interaction of HIV–1 Ribonuclease H with Polypurine Tract Containing RNA–DNA Hybrids", *Biochemistry* 1990, 29, 10141–10147.

Yannisch–Perron et al., "Improved M13 Phage Clonign Vectors and Host Strains: Nucleotide Sequences of the M13mp18 and pUC19 Vectors", *Gene,* 1985, 33, 103–119.

Zamecnik, P.C. et al., "Inhibition of Replication and Expression of Human T–cell Lymphotropic Virus Type III in Cultured Cells by Exogenous Synthetic Oligonucleotides Complementary to Virual RNA", PNAS, 1986, 83, 4143–4146.

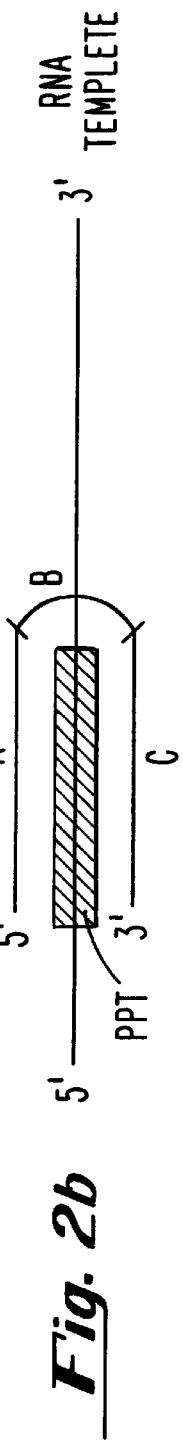
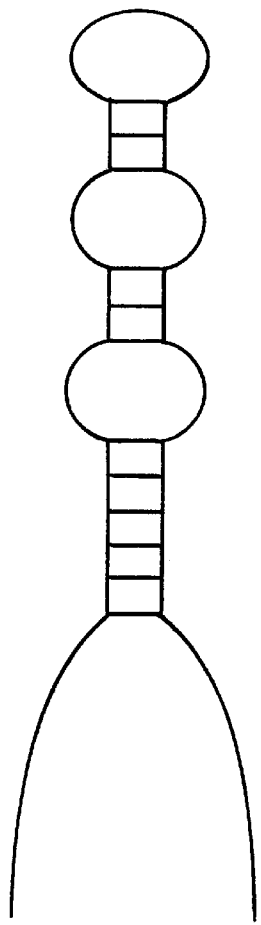
Fig. 2a
Fig. 2b
Fig. 3a
Fig. 3b

INHIBITION OF VIRUSES BY ANTISENSE OLIGOMERS CAPABLE OF BINDING TO POLYPURINE RICH TRACT OF SINGLE-STRANDED RNA OR RNA-DNA HYBRIDS

This is a continuation of PCT Application No. PCT/US93/09300, filed Sep. 29, 1993, which is a Continuation-In-Part of U.S. application Ser. No. 07/954,184, filed Sep. 29, 1992, now abandoned.

BACKGROUND OF THE INVENTION

This invention provides methods for inhibiting viral replication through the use of antisense and triplex-forming oligonucleotides. Antisense oligonucleotides are capable of specific hybridization with a nucleotide sequence of single-stranded RNA while triplex-forming oligonucleotides are known to be capable of specific hybridization with double-stranded DNA, double-stranded RNA, and DNA-RNA hybrids.

Triplex helix formation with double-stranded DNA is an approach known in the art for potential sequence-specific DNA recognition. An oligonucleotide is targeted against a specific region of double-stranded DNA, resulting in the formation of a triplex. Where the triplex forming oligonucleotide (TFO) has a sufficient length, such as 8–26 nucleotides, it is expected to bind to unique sites. It has been reported that sequence specific recognition of the major groove of DNA at homopurine.homopyrimidine sequences is achieved by homopyrimidine oligonucleotides. Sun et al., *Proc. Natl. Acad. Sci. USA*, July, 1991, 88, 6023–6027. The TFO may be either parallel or anti-parallel to the target DNA strand. Experimental methods have been devised for detection of triple helix formation. Maher et al., *Inhibition of DNA/Protein Interactions by Oligonucleotide-Directed DNA Triple Helix Formation: Progress and Prospects in Prospects for Antisense Nucleic Therapy of Cancer and AIDS*, 227–242 (1991).

All retroviruses and hepadna viruses, such as HIV and hepatitis, replicate by the conversion of an RNA template into DNA through the action of the enzyme, reverse transcriptase (RT). This enzyme copies the RNA template into a complementary DNA strand, giving rise to an RNA-DNA hybrid. The enzyme then degrades the RNA strand through its RNase H function and the DNA strand is copied into double-stranded DNA. Two primers are involved in the reverse transcription of viral RNA into double-stranded DNA. One of these primers is a polypurine tract (PPT) which allows initiation of the plus-strand DNA. K. Moelling, Minireview: *The RNase H of HIV-1*, Med. Microbiol. Lett. 1992, 1, 71–77. Apparently all known retroviruses such as Rous Sarcoma Virus, use polypurine tracts as primers.

Two PPT's are present in HIV; one is located within the coding region of the integrase gene and the other resides near the 3' long terminal repeat (LTR). The PPT is one of the most highly conserved regions among the known HIV-1 retroviral isolates, as illustrated in Tables 1A and 1B below. The nucleotides in the consensus sequences at which variations occur are indicated in lower case.

TABLE 1A

3' LTR PPT

| | |
|---|---|
| CONSENSUS | a AAa g AAa AGGGGGGACTGGAa GGGc |
| HIVLAI | A--AG--A-------------A---C |
| HIVNL43 | A--AG--A-------------A---C |
| HIVBRVA | A--AG--A-------------A---C |
| HIVSC | A--AG--C-------------A---C |
| HIVBAL1 | T--GA--A-------------A---C |
| HIVJRCSF | A--AG--A-------------A---C |
| HIVOYI | A--AG--A-------------A---C |
| HIVSF2 | A--AG--A-------------A---C |
| HIVSF162 | A--AG--A-------------A---T |
| HIVSF33 | A--AG--A-------------A---C |
| HIVHAN | A--AG--A-------------A---T |
| HIVRF | A--AG--A-------------T---C |

TABLE 1B

Integrase PPT

| | |
|---|---|
| CONSENSUS | AAAAGAAAAGGGGGGATTGGGGGg TA |
| HIVLAI | ----------------------G-- |
| HIVHXB2R | ----------------------G-- |
| HIVMN | ----------------------G-- |
| HIVJRCSF | ----------------------G-- |
| HIVOYI | ----------------------G-- |
| HIVSF2 | ----------------------A-- |
| HIVNYSCG | ----------------------G-- |
| HIVNL43 | ----------------------G-- |
| HIVHAN | ----------------------G-- |
| HIVRF | ----------------------G-- |

One targeted PPT consists of a sequence of 16 contiguous purines common to both the 3' LTR and the integrase gene: AAAAGAAAAGGGGGGA (SEQ ID NO: 1). The 16 contiguous purines are indicated in bold in the "Consensus" sequences above. The targeted PPT can also consist of a sequence of 26 nucleotides with all purines except for 2 pyrimidines present near the 3' end, i.e., AAAA-GAAAAGGGGGGACTGGAAGGGC (SEQ ID NO: 2). The two pyrimidines are underlined in the "Consensus" 3' LTR sequence above. The PPT region near the 3' LTR is essential for HIV-1 replication, as demonstrated by a non-infectious RT/RNase H mutant which cannot initiate plus-strand DNA synthesis at the PPT in vitro. B. Wohrl et al., *Mutations of a Conserved Residue within HIV-1 Ribonuclease H Affect Its Exo- and Endonuclease Activities*, J. Mol. Biol. 1991, 220, 801–818. It has also been demonstrated that RT/RNase H specifically generates a PPT RNA primer for plus-strand DNA synthesis in HIV-1. B. Wohrl & K. Moelling, *Interaction of HIV-1 Ribonuclease H with Polypurine Tract Containing RNA-DNA Hybrids*, Biochemistry 1990, 29, 10141–10147.

Antisense oligonucleotides have been targeted against HIV-1 viral RNA in a site adjacent to the primer binding site which is folded into a loop. Buck et al., *Phosphate-Methylated DNA Aimed at HIV-1 RNA Loops and Integrated DNA Inhibits Viral Infectivity*, Science 1990, 248, 208–212. This work did not involve the PPT, however.

The PPT region of HIV-1 has been targeted for the formation of a triple helix. Sun et al., *Triple-Helix Formation by α Oligodeoxynucleotides and α Oligodeoxynucleotide-Intercalator Conjugates*, Proc. Natl. Acad. Sci. 1991, 88, 6023–6027. Sun et al. synthesized a series of oligonucleotides having a single 16-nucleotide long sequence, TTTTCTTTTCCCCCCT (SEQ ID NO: 5), which were capable of binding the double-stranded DNA HIV PPT region in vivo. Thus, the prior art does not provide for the formation of a duplex or a triplex involving the PPT region at a stage of viral replication other than that of double-stranded DNA. Triplex formation with double-stranded DNA occurs through binding with a DNA homopurine strand in the major groove of the DNA duplex. Sun et al. Targeting double-stranded DNA presents a major limitation for designing viral drug therapies. Double-stranded viral DNA is present mainly in the nucleus of the infected cell and it is more difficult to deliver drug therapies into the nucleus. Contrastingly, single-stranded viral RNA and RNA-DNA hybrids are predominantly found in the cytoplasm. Therapeutics targeting single-stranded RNA, or RNA-DNA hybrids, provide a significant advantage over those targeting double-stranded DNA. Furthermore, unlike double-stranded viral DNA, single-stranded RNA and RNA-DNA hybrids are present prior to provirus formation and integration. Thus, therapeutics targeting single-stranded RNA and RNA-DNA hybrids could also provide greater protection against de novo infection.

SUMMARY OF THE INVENTION

The present invention provides methods of inhibiting RNA virus replication by the administration of an antisense oligonucleotide or a triplex forming oligonucleotide, or derivatives thereof, to a vertebrate infected with said virus wherein the oligonucleotide is capable of binding to single-stranded RNA or RNA-DNA hybrids containing a polypurine-rich tract. The present invention thus targets the earlier stages of viral replication before double-stranded DNA is formed. The antisense and triplex-forming oligonucleotides generally range in size from about 8 to about 54 nucleotides long, or longer, and may be modified according to methods known in the art. The oligonucleotides are capable of binding with at least a portion of the PPT region, however, the oligonucleotides may extend beyond the PPT. The nucleotides may match the PPT region exactly or may contain several mismatches.

A preferred embodiment of the instant invention provides methods for treating HIV infection whereby an effective amount of oligonucleotide, or derivative thereof, is administered to an infected vertebrate, preferably human.

In a further preferred embodiment, the present invention provides chimeric oligonucleotides capable of binding to a polypurine-rich tract of single-stranded viral RNA and forming a triplex, thereby preventing its reverse transcription into viral DNA. The chimeric oligonucleotides are of the general formula 5'-A-B-C-3' wherein segment A comprises a sequence complementary to PPT in parallel orientation, segment B comprises a linker, and segment C comprises a sequence complementary to PPT in antiparallel orientation.

BRIEF DESCRIPTION OF THE DRAWINGS

FIGS. 2A–2B schematically depict the oligonucleotides of the present invention and how they form triplexes with single-stranded RNA.

FIGS. 3A–3B depict the TFO A sequence and structure, respectively.

DETAILED DESCRIPTION OF THE INVENTION

Figure 1:
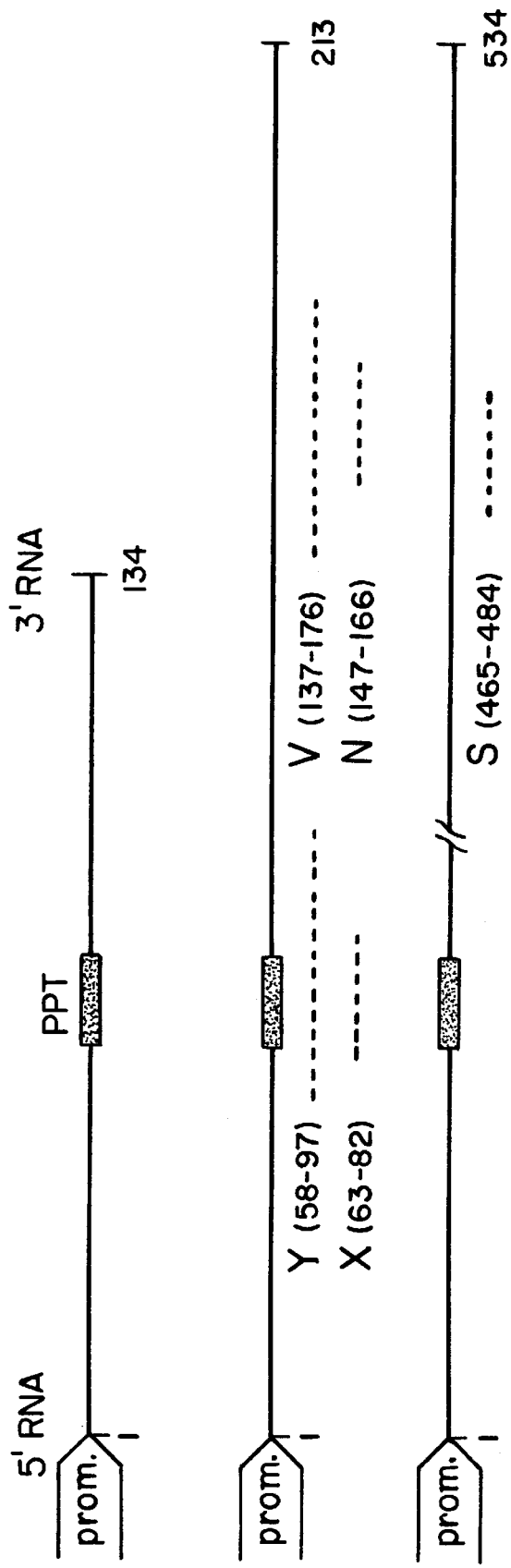
FIG. 1 is a schematic diagram of the constructs used in the Examples.

The present invention provides methods of inhibiting RNA virus replication by the administration of an antisense or triplex-forming oligonucleotide, or derivative thereof, to a vertebrate wherein the oligonucleotide is capable of binding to single-stranded RNA or RNA-DNA hybrids containing a polypurine-rich tract (PPT). The PPT serves as a primer for reverse transcription of viral RNA into double-stranded DNA and is one of the most highly conserved regions among known HIV-1 viral isolates. The PPT region is necessary for HIV-1 replication. Single-stranded RNA and RNA-DNA hybrids are structures which occur at various points in viral replication. For example, retroviruses begin with a single-stranded RNA, which is reverse transcribed into DNA, thus forming an RNA-DNA hybrid. The RNA strand is then degraded by the RNase H function of reverse transcriptase and the remaining DNA strand is duplicated to form double-stranded DNA.

Several retroviruses and viruses which replicate via an RNA template which are capable of infecting vertebrates are known, including hepatitis and HIV. The RNA viruses which are the subject of the present invention have one or more polypurine tracts (PPTs), highly conserved regions consisting essentially of purines.

One embodiment of the present invention provides an antisense oligonucleotide directed against a PPT on single-stranded viral RNA. The single strand of RNA is used by the virus as a template for reverse transcription, and one object of the invention is to interfere with viral replication at this stage through the formation of a duplex at the polypurine-rich tract. The invention thus provides methods for inhibiting pathogenesis by administering an antisense oligomer capable of forming a duplex with the PPT of the RNA strand whereby the duplex prevents elongation of cDNA synthesis. The duplex can be detected, for example, by treatment with RNase H which specifically cleaves the RNA-DNA hybrid region where the antisense oligomer is bound.

A further aspect of the present invention targets the formation of RNA-DNA hybrids during viral replication. These naturally occurring hybrids form upon reverse transcription of the RNA template into a DNA strand and these hybrids are thus essential for replication in RNA viruses. One purpose of this invention is to interfere with viral replication at this stage through the formation of a triplex with the RNA-DNA hybrid. The invention provides methods for inhibiting pathogenesis by administering an oligomer capable of forming a triplex with the hybrid at the PPT and thus protecting the PPT from RNase H digestion.

In yet a further aspect of the present invention, oligonucleotides directed against PPT on single-stranded RNA are provided which are capable of forming triplexes with the single-stranded RNA in the following general orientations: R-R-D or D-R-D. Oligonucleotides capable of forming D-R-R triplexes are also contemplated. The middle "R" represents the viral RNA template. The remaining "R's" and "D's" represent the "A" and "C" segments of the oligonucleotides of the invention in the general binding orientation "A-R-C" with the RNA template. See FIG. 2b.

The oligonucleotides of the present invention are capable of protecting the PPT region, whether in the form of single-stranded RNA or RNA-DNA hybrid. The binding of the triplex-forming oligonucleotide to the PPT is measured by protection from RNase H digestion, since RNase H degrades RNA only when in RNA-DNA hybrids. TFO binding to a double-stranded DNA, in contrast, affords protection from DNase I digestion. Increased premature termination of cDNA synthesis at the PPT indicates antisense binding to single-stranded RNA.

Antisense or TFO binding in all of the above situations may also be measured in several other ways. For example, altered migration properties as measured by gel shift, physical chemical parameters such as melting temperatures, and by footprinting. Since the PPT region is highly conserved across known HIV-1 viral isolates, the same oligonucleotide may be administered to combat suspected infections of all of the known isolates.

It will be understood by those skilled in the art that PPT regions in viruses other than those specifically disclosed are contemplated. In choosing oligonucleotides which target PPT regions, a PPT region conserved among viral isolates can be identified by a computer-aided comparison of known nucleotide sequences among known isolates of a virus. The sequence to be identified is a polypurine sequence of at least about 8 nucleotides long, and preferably at least about 26 nucleotides long, wherein at least about 50%, and preferably about 80%, of the nucleotides are identical across the viral isolates and wherein at least about 70%, and preferably at least about 80%, and more preferably at least about 90%, of the nucleotides are purines, and wherein at least one PPT acts as a primer for reverse transcription.

The oligonucleotide need not match the target sequence exactly; it may span only a portion of the PPT and some mismatches may be included. The length of the oligonucleotide is preferably from about 8 to about 54 nucleotides long. The oligonucleotides should be a size which is long enough to bind specifically to the target PPT region, but not too large to prohibit entry into a cell. It will be understood that an antisense oligonucleotide may be longer than a triplex-forming oligonucleotide since the former hybridizes via Watson-Crick bonds which may extend further than the polypurine rich region while the latter forms Hoogsten-type bonds which are most efficiently formed in a polypurine rich region.

The PPT region is essential for HIV-1 replication, as demonstrated by a non-infectious RT/RNase H mutant which cannot initiate plus-strand synthesis at the PPT in vitro. B. Wohrl et al., *J. Mol. Biol.* 1991, 220, 801–818. Accordingly, embodiments of the invention whereby the oligonucleotide or derivative is targeted against the PPT region of HIV-1 are preferred.

The binding of the oligonucleotide to the target PPT sequence may have several related meanings. The present invention comprehends binding of an oligonucleotide or derivative with at least one portion of a PPT. It will be understood that in one embodiment of the present invention, the oligonucleotide or derivative will bind with single-stranded RNA in a Watson-Crick fashion so as to form, locally, a heteroduplex between the RNA and the oligonucleotide or derivative. This heteroduplex is capable of increasing premature termination of cDNA synthesis at the PPT and therefore inhibits viral replication.

An increase in premature termination of cDNA synthesis can be measured, for example, by incubating with reverse transcriptase for about 15 minutes the following: a viral RNA substrate, spanning the region containing the PPT and preferably about 40 to about 400 nucleotides long, the oligonucleotide to be tested, preferably 1 to 50-fold excess over the RNA substrate, and radiolabeled nucleotides. See for example, Worhl and Moelling, *Interaction of HIV-1 Ribonuclease H with Polypurine Tract Containing RNA-DNA Hybrids, Biochemistry*, 1990, 29, 10141–10147. At least about a 50% increase in premature termination of cDNA synthesis at the PPT, as determined by gel electrophoresis, indicates a significant increase in premature termination; a substantially complete blocking of cDNA synthesis, preferably at least about 90% and more preferably approaching 100% is preferred.

It will also be understood by those skilled in the art that the triplex may be formed, for example, by pairing of the purine strand to a complementary pyrimidine strand where, e.g., a C is used in the triplex-forming oligomer for every G in the purine strand and a T is used for every A, and complementary nucleotides are used for non-purines. Alternatively, a G may be used for every GC pair and a T for every AT base pair. See WO 90/06934 (Hogan, 1990). The term "triplex-forming oligonucleotide" in the present context is meant to include both of these alternatives. The binding may occur in parallel or anti-parallel orientation. The triplex results in substantial protection from RNase H where RNA-DNA hybrids are involved and likewise prevents viral replication.

In yet another aspect of the present invention, viral replication is inhibited using a chimeric oligonucleotide of the formula 5'-A-B-C-3'. "A" comprises a segment complementary to PPT on single-stranded viral RNA, in parallel orientation. "B" comprises a linker of at least two to three, and preferably four, nucleotides. Preferably, the linker comprises four nucleotides. More preferably, the four nucleotides comprise thymidine. "C" comprises a segment substantially complementary to PPT, in anti-parallel orientation. Since the complementarity of segment A of the oligonucleotide facilitates binding of "A" to the PPT portion of the single-stranded RNA in parallel orientation, and the complementarity of sequence C facilitates the binding of "C" to PPT in an anti-parallel orientation, use of a linker segment—B—connecting segments A and C enables a single oligonucleotide to form a triplex with single-stranded RNA. See FIGS. 2a and 2b.

Heretofore, triplexes discussed in the literature were formed with double-stranded DNA. The formation of triplexes using single-stranded nucleic acids and, more specifically, between single-stranded nucleic acids and a single oligonucleotide, has not been disclosed.

The chimeric oligonucleotides of the present invention facilitate formation of "A-R-C" triplexes, with "R" representing the single-stranded RNA. Triplex formation occurs at the single-stranded RNA stage of viral reproduction. Thus, inhibition at a much earlier stage in the replication cycle is facilitated which, in turn, affords more complete inhibition at a lower concentration of oligonucleotide. Use of a single oligonucleotide which binds to single-stranded RNA also ensures greater bioavailability in vivo for therapeutics. Furthermore, the RNA can be targeted in the cytoplasm and at two different stages—before the RNA enters the nucleus and immediately after it exits the nucleus—increasing the potential for more effective inhibition. With prior triplex forming methods double-stranded DNA was targeted. Not only does accessibility of the DNA in the nucleus present an additional barrier for potential therapeutics, but also it is more difficult to intercalate a third strand into a pre-existing double-stranded DNA.

Segment A of the chimeric oligonucleotides of the present invention is generally at least 8, preferably 16, and more preferably 25 nucleotides long. Longer nucleotide segments are also contemplated. Greatest inhibition is observed when the sequence is identically complementary with at least 16 nucleotides of the PPT region. However, mismatches of between 10–20% within a region of complementarity are acceptable. The nucleotides of segment A can consist of ribonucleotides, deoxyribonucleotides, or, most preferably, ribonucleotide or deoxyribonucleotide derivatives with backbone modifications wherein the phosphodiesters are replaced by phosphorothioates.

Segment B is generally a linker consisting of at least 2–3, and preferably four, nucleotides. In the examples which follow, a linker consisting of four thymidines was specifically utilized.

Segment C is generally at least 8, preferably 16, and most preferably 25 nucleotides long. Longer nucleotide segments are also contemplated. Segment C is substantially complementary to the PPT region in anti-parallel orientation. In the examples which follow, segment C comprises deoxyribonucleotides. Ribonucleotides are also contemplated. Again, mismatches of between 10–20%. in the region of complementarity can be tolerated.

Several of the oligonucleotides tested conferred 100% protection on the single-stranded RNA. One of the oligonucleotides did not exhibit triplex formation in the tests utilized, but inhibited RNA degradation 100%. Another oligonucleotide tested formed a "pseudocircle" due to complementary tails. The pseudocircle conferred 80% protection against RNA degradation. The oligonucleotides were added in micro-nanomolar amounts.

Substantial protection against RNase H degradation can be measured, for example, by incubating at 37° C. overnight the following: a radiolabeled RNA substrate, preferably about 100 to 400 nucleotides long, a DNA substrate, preferably about 8 to about 40 nucleotides long, both of which include the PPT, and the antisense oligonucleotide to be tested, in an amount which is preferably about 2 to about 100-fold in excess of the RNA substrate. The mixture is then incubated for about 30 minutes at 37° C. with RNase H in RNase H buffer with a substrate to enzyme ratio of about 4 to 1. See, for example, Worhl and Moelling, *Interaction of HIV-1 Ribonuclease H with Polypurine Tract Containing RNA-DNA Hybrids, Biochemistry,* 1990, 29, 10141–10147 and Wohrl et al., *J. Mol. Biol.* 1991, 220, 801–818.

It is known that RNase H preferentially cleaves at two sites within the PPT, at nucleotides 72 and 79. Worhl and Moelling, *Biochemistry,* 1990, 29, 10141–10147. Substantial protection against RNase H digestion is measured by the reduction of at least one cleavage product by at least about 50% and preferably at least about 80%, as determined by gel electrophoresis and using a control lane of the same reactants with RNase H. This measurement can be made, for example, by densitometric scanning.

The same oligonucleotide or derivative targeted against a PPT present in RNA may also be capable of forming a triplex with the PPT in a double-stranded DNA copy, thus protecting the PPT region in double-stranded DNA from DNase I digestion. However, such cannot be assumed due to chemical and structural differences between RNA and DNA. A triplex with double-stranded DNA would presumably prevent viral transcription since it occurs at a stage where the virus has already replicated its RNA genome into a double-stranded DNA copy. The double-stranded DNA stage is thus unlike the single-stranded RNA and RNA-DNA hybrid stages above which may arise before viral replication is complete. Intervention at the earlier stage is preferable since it should confer an advantage in combatting infection by inhibiting viral replication. Further, the targets are present in the cytoplasm, not in the nucleus.

The oligonucleotides may be synthetic deoxyribonucleotides, ribonucleotides, combinations (chimeras), or derivatives thereof. The use of ribonucleotide derivatives has been reported by Shibahara et al., *Nucleic Acids Research* 1989, 17, 239–252. A person skilled in the art is capable of synthesizing oligonucleotides. See for example, Gait, M. J., ed. (1984) *Oligonucleotide Synthesis* (IRL, Oxford).

Derivatives contemplated include modifications of the nucleotides which increase bioavailability by enhancing stability to nuclease attack and/or increasing cellular uptake. For example, the modification of the nucleotide backbone bonds from phosphodiesters to phosphorothioates confers greater stability against nuclease attack. Phosphorothioates, i.e., the substitution of a sulfur atom for a phosphate oxygen in the internucloetide phosphodiester linkage, are stable to nuclease cleavage and soluble in lipid. Lipid solubility can be important for bioavailability, as discussed further below regarding liposomes. Preferably, only the two terminal bonds at either, or both, ends of the oligonucleotides are modified. In this manner, stability is increased without foresaking cellular uptake. The oligonucleotides can also be protected from exonuclease attack through the addition of amino groups at the ends. Derivatives such as methylphosphonates, phosphotriesters, phosphorothioates and phosphoroamidates are also contemplated. Additionally, beta-anomers may be replaced with alpha-anomers. Sun et al., *Triple-Helix Formation by a oligodeoxynucleotides and a Oligodeoxynucleotide-Intercalator Conjugates, Proc. Natl. Acad. Sci.* 1991, 88, 6023–6027. See also C. A. Stein & J. S. Cohen, *Oligodeoxynucleotides as Inhibitors of Gene Expression: A Review, Cancer Research* 1988, 48, 2659–2668.

While any length oligonucleotide may be utilized, sequences shorter than 15 bases may be less specific in hybridizing to the target and may be more easily destroyed by enzymatic degradation. The chimeric oligonucleotides of the present invention having the formula 5'-A-B-C-3' consist of at least 20 nucleotides or more. Conversely, the size of the oligonucleotide may limit its ability to enter the target cell. Large oligonucleotides may be somewhat less effective in interfering with expression because of decreased uptake by the target cell. However, carriers can be employed to further increase the uptake of the oligonucleotides.

It is generally preferred to administer the oligonucleotides and their derivatives to an infected individual in accordance with this invention internally, such as orally, intravenously or intramuscularly. Other forms of administration, such as transdermally, topically, or intralesionally may also be useful. Inclusion in suppositories can also be useful. Use of the oligonucleotides and their derivatives in prophylaxis is also likely to be useful. Use of pharmaceutically acceptable carriers is also preferred for some embodiments.

Pharmaceutical compositions of this invention comprise a pharmaceutically acceptable carrier or diluent and an effective quantity of one or more of the oligonucleotides or their derivatives, or an acid or base salt thereof. The carrier or diluent may take a wide variety of forms depending on the form of preparation desired for administration, e.g., sublingual, rectal, nasal, oral, or parenteral.

In preparing the compositions in oral dosage form, any of the usual pharmaceutical media may be employed, for example, waters, oils, alcohols, flavoring agents, preservatives, and coloring agents, to make an oral liquid preparation (e.g., suspension, elixir, or solution) or with carriers such as starches, sugars, diluents, granulating agents, lubricants, binders, and disintegrating agents, to make an oral solid preparation (e.g., powder, capsule, or tablet).

Controlled release forms or enhancers to increase bioavailability may also be used. Because of their ease in administration, tablets and capsules represent the most advantageous oral dosage unit form, in which case solid pharmaceutical carriers are employed. If desired, tablets may be sugar coated or enteric coated by standard techniques.

For parenteral products, the carrier will usually be sterile water, although other ingredients to aid solubility or as preservatives may be included. Injectable suspensions may also be prepared, in which case appropriate liquid carriers and suspending agents can be employed.

The oligonucleotides and their derivatives can also be administered locally at a lesion by topical application of a solution or cream.

Alternatively, the oligonucleotides or their derivatives may be administered in liposomes or microspheres (or microparticles). Incorporation of the oligonucleotides into liposomes can improve the bioavailability of the oligonucleotides for therapy. Furthermore, incorporation of the oligonucleotides into immunoliposomes, such as discussed in Uhlmann, et al., "Antisense Oligonucleotides: A New Therapeutic Principles", *Chemical Reviews,* Volume 90, No. 4, pages 544–584, June 1990 (incorporated herein by reference) can help to specifically target the oligonucleotides. Methods for preparing liposomes and microspheres for administration to a patient are known to those skilled in the art. U.S. Pat. No. 4,789,734 describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes", *Drug Carriers in Biology and Medicine,* pp. 287–341 (Academic Press, 1979). Microspheres formed of polymers are well known to those skilled in the art, and can be tailored for passage through the gastrointestinal tract directly into the bloodstream. Alternatively, the nucleotides or their derivatives can be incorporated and the microspheres, or composite of microspheres, implanted for slow release over a period of time, ranging from days to months. See, for example, U.S. Pat. Nos. 4,906,474, 4,925,673 and 3,625,214.

Tests show that the best results are achieved when the oligonucleotides are administered in an excess of at least about 2-fold, preferably at least about 10-fold, to the target single-stranded RNA or RNA-DNA hybrid. An optimal dosage for an infected individual will, of course, depend on the size of the individual and the type and extent of infection. Generally, however, the oligonucleotides or their derivatives should be active when administered parenterally in amounts above about 0.1 to about 30 mg/kg body weight. Effective doses by other routes of administration should generally be those which result in similar blood level to i.v. doses above about 0.1 to about 30 mg/kg. Uhlmann et al. reported that multiple administration of small amounts of oligonucleotide appeared to have a more beneficial effect than a single large dose. Anfossi, et al., *Proc. Natl. Acad. Sci. USA,* 1989, 3379–3383 reported the application of oligonucleotides to cell culture in three doses with an inhibitory effect on proliferation of human myeloid leukemia cell lines. Others reported positive results in vivo in mice using a regimen of oligonucleotide dispensed continually over a period of 7–14 days. Ratajczak, et al., *Proc. Natl. Acad. Sci. USA,* December 1992, 89, 11823–11827.

In Ratajczak et al., phosphorothioate-modified antisense oligonucleotides against the c-myb protooncogene were utilized. Mice received a total of 5 mg/kg body weight oligonucleotide per day over a dosage period of 7–14 days. Doses were administered at 1 microliter per hour, subcutaneously into a paraspinal pocket. Leukemic mice receiving the therapy lived 3.5 times longer than leukemic mice not receiving the therapy. Mice were induced with human leukemia.

The criteria for assessing response to therapeutic modalities employing these nucleotides, and, hence, effective dosages of the nucleotides of this invention for treatment, are dictated by the specific condition and will generally follow standard medical practices. Overall, it is preferred to administer to patients suspected of suffering from RNA virus disease states with effective amounts of oligonucleotides or derivatives, in either native form or suspended in a carrier medium in amounts and upon treatment schedules which are effective to reduce the symptomology of disease. It is within the scope of a person's skill in the art to determine optimum dosages and treatment schedules for such treatment regimens.

The following non-limiting examples are meant to illustrate several embodiments of the invention.

EXAMPLES

EXPERIMENTAL PROCEDURES

Materials.

Restriction enzymes, bacterial alkaline phosphatase, and the vanadyl ribonucleoside complex (VRC) were purchased from BRL, Berlin, West Germany. HaeIII-restricted pBR322 DNA, T4 polynucleotide kinase, T4 DNA ligase, RNase-free DNase I, *E. coli* RNase H, 2'3'-dideoxynucleoside triphosphates (dNTPs) were obtained from Boehringer Mannheim, Mannheim, Best Germany. RNasin was purchased from Promega Biotech, Heidelberg, West Germany. Sequencing reactions were performed with the Sequenase kit from USB, Cleveland, Ohio. AMV RT and the vector pTZ19R harboring the T7 promoter were obtained from Pharmacia, Uppsala, Sweden. Radiolabeled compounds $[\gamma^{-32}P]$ ATP (3000 Ci/mmol), $[\gamma^{-32}P]$UTP (0.400 Ci/mmol), $[\alpha^{-32}S]$ dATPαS (>1000 Ci/mmol), and $[^3H]$ TTP (42 Ci/mmol) were purchased from Amersham Buchler, Braunschweig, West Germany. The RNA transcription kit, T7 RNA polymerase, and AMV reverse transcriptase sequencing kit were purchased from Stratagene, Heidelberg, West Germany. DNA oligonucleotides were synthesized on an Applied Biosystems oligonucleotide synthesizer and were purified by HPLC prior to use.

DNA Manipulations.

Restriction endonuclease cleavage, DNA isolation, ligation, end labeling of DNA, and transformations were performed as described in Maniatis et al., *Molecular Cloning: A Laboratory Manual* (Cold Spring Harbor, N.Y. 1982).

Plasmid Constructions.

The 474 base pair long PvuII fragment from the HIV-1 provirus clone BH10 (supplied by Dr. R. C. Gallo) including the polypurine tract (PPT) was cloned into the SmaI site of the T7 transcription vector PTZ19R to yield plasmid pTZp8, which was further used in RNA transcription assays. The same PvuII fragment was cloned in both orientations into DNA of the phage M13mp18. For isolation of DNA, the constructs were transformed into the *E. coli* K12 strain JM109 according to Yannisch-Perron et al., *Gene,* 1985, 33, 103–119. Plasmids pKJ2 and pKJ11 were derived from pTZp8 as indicated in FIG. 1.

In Vitro Transcription with Plasmids pTZp8, pKJ2 and pKJ11.

A total of 1 μg of DNA of plasmid pTZp8, pKJ2 or pKJ11 was linearized with EcoRI and, after proteinase K treatment and phenol/chloroform extraction, was transcribed by T7 RNA polymerase according to the conditions described in the Stratagene RNA transcription kit. Thus, an RNA of 534 bases in length was synthesized including the PPT and flanking regions where pTZp8 was used and an RNA of 213 or 134 bases where pKJ2 or pKJ11 was used (see FIG. 1). High specific RNA probes were uniformly labeled with 40 μM UTP and 50 μCi of $[\alpha^{-32}P]$UTP, and low specific RNA was obtained with 200 μM UTP and 50 μCi of $[\alpha^{-32}P]$UTP.

Purification of HIV-1 RT/RNase H.

The bacterially expressed recombinant RT/RNase H was purified as described previously with a poly (U) -Sepharose instead of an Aga(rC) column according to Hansen et al., *J. Biol. Chem.* 1987, 262, 12393–12396 and Hansen et al., EMBO J. 1988, 7, 239–243. One unit of purified HIV-1 RT/RNase H catalyzes the incorporation of 13 pmol of [$^3$H]TMP into acid-insoluble products in 10 minutes at 37° C. with poly(Ra)●(dT)$_{10}$ as template/primer. The concentration of the enzyme corresponds to about 1 µL per unit.

Sequencing Reactions.

Sequencing reactions were carried out by using the dideoxy sequencing kit from USB according to the manufacturer's instructions except with a $^{32}$P-end-labeled oligonucleotide primer in some reactions. Aliquots were analyzed on 8% or 10% TEE-urea-polyacrylamide gels.

EXAMPLE 1 SINGLE-STRANDED RNA

HIV-1 viral RNA was transcribed in vitro from a construct containing a T7 promoter along with the PPT, which consists of the sequence: AAAAGAAAAGGGGGGA (SEQ ID NO: 1) or AAAAGAAAAGGGGGGACTGGAAGGGC (SEQ ID NO: 2) when extended within the 3' LTR and 2 nonpurines are included. The viral RNA, corresponding to pKJ2, consisted of 134 nucleotides. A $^{32}$P end-labeled antisense oligonucleotide was hybridized with the RNA. The cDNA reaction products were analyzed on 10% polyacrylamide TEE-urea gels. Details of the procedure are as follows:

RNase H Reaction Coupled with cDNA Elongation.

To the standard reaction mixture described in Example 2 below were added a 125 µM quantity of one of the ddNTPs and each of the other three dNTPS and 4 units of HIV-1RT. The reactions were started by the addition of approximately 3 pmol of hybrid RNA (low specific activity) and treated as described above. To check for cDNA elongation, the same test was carried out, except with unlabeled in vitro transcribed RNA hybridized to a 10:1 mixture of unlabeled to labeled oligonucleotide. Aliquots were analyzed by electrophoresis on 10% TEE-urea-polyacrylamide gels.

RNase H Reaction and Oligonucleotide Extension Assays of RNase H Treated Model Substrates X and Y.

The RNase H reaction was carried out in a total volume of 500 µL in RNase H buffer containing 1000 units of RNasin and 25 units of HIV-1RT/RNase H. After the reaction was started by the addition of 8 pmol of an unlabeled RNA-DNA oligonucleotide hybrid, the sample was divided into five aliquots of 100 µL and incubated for 30 minutes at 37° C., and the reaction was stopped at 95° C. for 5 minutes. The samples were placed on ice and to each was added 10 units of DNase I to remove the DNA oligonucleotide. After 10 minutes, the samples were incubated further at 37° C. for 10 minutes. The reactions were stopped at 95° C. for 10 minutes. A $^{32}$P-end-labeled DNA oligonucleotide primer N complementary to a sequence 66–86 bases downstream of the PPT was annealed to the cleaved RNA and the primer extended up to the RNase H cleavage site in a total volume of 15 µL in 1×RT buffer (Stratagene sequencing kit) by means of 7 units of AMV RT (Stratagene sequencing kit), 20 units of RNasin, and dNTPs to 330 µM. After 1 hour at 42° C., the reaction was stopped with 5 µL of formamide buffer included in the kit. Aliquots were analyzed by electrophoresis on an 8% TBE-urea-polyacrylamide gel together with dideoxy sequencing ladders generated with the same $^{32}$P-end-labeled DNA oligonucleotide primer on a single-stranded M13 DNA template harboring the corresponding DNA fragment.

RNase H Reaction and Reverse Transcription Using an M13 RNA Hybrid as Substrate.

A total of 2.5 µg of in vitro transcribed RNA and 8 µg of the M13 single-stranded DNA harboring the complementary fragment were hybridized in RNase H buffer in a total volume of 25 µL by heating the mixture to 80° C. and cooling it slowly (1–2 hours) to room temperature. The RT/RNase H reaction was carried out in a total volume of 50 µL in RNase H buffer containing 50 units of RNasin, 10 units of HIV-1 RT/RNase H, and a 150 µM quantity of each DNTP. The reaction was started by the addition of 25 µL of the hybridization mixture, the mixture was incubated for 40 minutes at 37° C., and the reaction was terminated by heating the sample to 95° C. for 3 minutes. After treatment with 0.3M NaOH at 65° C. for 20 minutes, ammonium acetate (pH 4.8) was added to 3M, and the products were precipitated with 4 volumes of absolute ethanol and washed three times with 70% ethanol to remove salt and free nucleotides. An oligonucleotide extension assay was carried out with the $^{32}$P-end-labeled DNA oligonucleotide N described above in 1×Sequenase buffer (Sequenase Kit) in a total volume of 20 µL. The mixture contained 5 mM DTT, a 250 µM quantity of each dNTP, and 7.5 units of Sequenase and was incubated for 40 minutes at 37° C. The reaction was stopped by the addition of 5 µL of formamide buffer included in the Sequenase kit. Electrophoresis was performed on a 10% gel along with dideoxy sequencing ladders generated on the corresponding M13 DNA template with the unlabeled DNA primer N and [α-$^{35}$S]dATPαS. See Wohrl and Moelling, *Interaction of HIV-1 Ribonuclease H with Polypurine Tract Containing RNA-DNA Hybrids*, Biochemistry 1990, 29, 10141–10147 and B. Wohrl et al., *Mutations of a Conserved Residue within HIV-1 Ribonuclease H Affect Its Exo- and Endonuclease Activities*, J. Mol. Biol. 1991, 220, 801–818.

The results indicated that premature termination of cDNA synthesis at homopolymeric stretches of the RNA template is most prominent at the PPT. This natural premature termination can be further increased by the addition of an antisense oligonucleotide which binds to the PPT region. An antisense 20-mer, AGTCCCCCCTTTTCTTTTAA (SEQ ID NO: 10) and an antisense 40-mer, TGAATTAGCCCTTC-CAGTCCCCCCTTTTCTTTTAAAAAGT (SEQ ID NO: 9), both of which cover the PPT, were used and led to complete (100%) blocking of cDNA synthesis with two to three prominent stops. An antisense 20-mer outside the PPT region, CCGCCCAGGCCACGCCTCCC (SEQ ID NO: 11), was much less inhibitory (20–50%) for cDNA elongation than the 20-mer covering the PPT (100%).

TABLE 2

Y (40-mer) = 58–97: (SEQ ID NO:9)
 TGAATTAGCCCTTCCAGTCCCCCCTTTTCTTTTAAAAAGT

X (20-mer) = 63–82: (SEQ ID NO: 10)
 AGTCCCCCCTTTTCTTTTAA

CONTROL = S (20-mer) = 465–484: (SEQ ID NO: 11)
 CCGCCCAGGCCACGCCTCCC

EXAMPLE 2 pJK11 RNA-DNA HYBRIDS

Viral RNA was transcribed in vitro from a construct containing a T7 promoter along with the PPT, and the RNA was radiolabeled. The viral RNA, corresponding to pKJ11, consisted of 213 nucleotides. A DNA oligomer consisting of 40 oligonucleotides, TGAATTAGCCCTTCCAGTC-CCCCCTTTTCTTTTAAAAAGT (SEQ ID NO: 9), spanning the PPT region was synthesized in vitro and was utilized as a strand in the RNA-DNA hybrid. Two 25-mers, TFO 1 and TFO 1' and two 16-mers, TFO 4 and TFO 4', the triplex-forming oligonucleotides (TFOs), were also synthesized in vitro. The TFO's were added at 10-Fold and 100-Fold molar excess.

TABLE 3

TFO 1 25-mer parallel polypyrimidine: (SEQ ID NO: 3)
TTTTCTTTTCCCCCCTGACCTTCCC

TFO 1' 25-mer parallel mixed purines & pyrimidines: (SEQ ID NO: 4)
TTTTGTTTTGGGGGGTGTGGTTGGG TFO 4 16-mer parallel polypyrimidine: (SEQ ID NO: 5)
TTTTCTTTTCCCCCCT TFO 4' 16-mer parallel mixed purines & pyrimidines: (SEQ ID NO: 6)
TTTTGTTTTGGGGGGT The same RNA-DNA hybrid substrate but without a TFO was used as a control.

Triplex formation was performed under physiological conditions using 10 mM magnesium, 80 mM sodium chloride, spermidine, and a pH of 7.2. RNA and DNA were preheated to 96° C. and allowed to cool slowly. The preheating in this and subsequent examples was to prevent the formation of secondary structures by the "naked" nucleic acids in vitro which may inhibit binding. In vivo, melting proteins, such as histones, prevent the formation of interfering secondary structure. The incubation was performed overnight at 37° C. to allow triplex formation. In general, RNase H cleavage of RNA-DNA oligonucleotide hybrids was measured as follows:

Standard reactions were carried out in a total volume of 20 µL in RNase H buffer (50 mM Tris-HCl, pH 7.8, 40 mM NaCl, 1 mM MgCl$_2$, 2 mM DTT) containing 20 units of RNasin. A total of 0.2 unit of HIV-1 RT/RNase H, 3 units of AMV RT/RNase H, or 4 units of RNase H from *E. coli* was added. (Unit definitions of AMV RT and RNase H from *E. coli* are according to the descriptions given by the manufacturers.) Reactions were started by the addition of 0.2 pmol of the RNA (high specific activity) prehybridized in the presence of a 20–25-fold molar excess of the corresponding DNA oligonucleotide. The mixture was incubated for 30 minutes at 37° C., and the reactions were terminated by the addition of 6 µL of urea loading buffer (7M urea in 1×TBE, 0.1% each xylene cyanol and bromophenol blue). Aliquots were analyzed by electrophoresis on a 10% TBE-urea-polyacrylamide gel. See also Maher et al., *Biochemistry* 1990, 29, 8820–8826 for details of the procedure.

Two concentrations of the TFO were used; 10- and 100-fold excess compared to the hybrid and the TFO's were incubated with recombinant RT/RNase H.

All of the TFO's shown in Table 3 led to substantial protection against RNase H digestion. Nonetheless, a 25-mer, sequence, TFO 1', was two- to four-fold more efficient than a 16-mer, TFO 4', at concentrations of both 10- and 100-fold excess. TFO 4' led to some effect, albeit two-fold less efficient, at 10-fold molar excess. The TFO's which had a G for every G-T pair and a T for every A-T pair (TFO 1' and TFO 4') had greater efficiency than the polypyrimidine TFO's (TFO 1 and TFO 4).

A 213-nucleotide long RNA corresponding to pKJ11 was end-labeled with $^{32}$P in vitro. This RNA includes the PPT. The RNA was mixed with the PPT-covering DNA oligo-nucleotide in a ratio of 1 to 2 or 1 to 10, heated to 100° C. and allowed to slowly cool. The mixture was incubated with the TFO oligonucleotide at 37° C. overnight. Three different TFO's were used, designated TFO 1, TFO 2 and TFO 3.

TABLE 4

TFO 1 25-mer parallel polypyrimidine: (SEQ ID NO: 3)
TTTTCTTTTCCCCCCTGACCTTCCC

TFO 2 25-mer parallel polypurine: (SEQ ID NO: 7)
AAAAGAAAAGGGGGGACTGGAAGGG

TFO 3 25-mer anti-parallel polypyrimidine: (SEQ ID NO: 8)
CCCTTCCAGTCCCCCCTTTTCTTTT Incubation with purified recombinant RNase H was performed under standard assay conditions as published in Wohrl, B et al., *Mutations of a Conserved Residue within HIV-1 Ribonuclease H Affect Its Exo- and Endonuclease Activities, J. Mol. Biol.* 1991, 220, 801–818. Triplex formation was performed under physiological conditions using 10 mM magnesium, 80 mM sodium chloride, spermidine, and a pH of 7.2. RNA and DNA were preheated to 96° C. and allowed to cool slowly. The incubation was performed overnight at 37° C. to allow triplex formation. The incubation period with RNase H was performed at 37° C. for 15 minutes. See Example 2 above and Maher et al., *Biochemistry* 1990, 29, 8820–8826 for details of the procedure.

All TFO's in Table 4 showed substantial RNase H protection when compared to the control, wherein the hybrid substrate without a TFO was incubated with RNase H, but TFO's 2 & 3 showed greater protection. Protection against RNase H digestion indicates the formation of a triplex which would be expected to interfere with viral replication in vivo, given the results obtained with RT/RNase H mutants.

EXAMPLE 3 pJK2 RNA-DNA HYBRIDS

In vitro transcribed, 5'end-labeled pKJ2 RNA of 134 nucleotides in length was hybridized with a 10-fold excess of a 40-mer deoxyribonucleotide complementary to the PPT region. Volkmann, et al., *Biochimie*, 1993, 75, 71–78. Hybridizations were carried out in 25 mM Tris-acetate buffer (pH 6.8) containing 50 mM NaCl, 10 mM β-mercapotoethanol and 0.4 mM spermine hydrochloride. The mixture was incubated for 3 minutes at 90° C., then cooled slowly to room temperature. For triplex-formation, 1 pmol hybrid substrate was incubated with either 10 or 100 pmol oligodeoxynucleotide overnight at 37° C. Finally, each sample was treated with 12 ng enzyme in 10 microliters RNase H-standard buffer (see Example 2) for 30 minutes at 37° C. RNase H cleavage reaction was stopped by incubation at 96° C. for 2 minutes. Samples were ethanol-precipitated and analyzed on 10% polyacrylamide-TEE-urea gel. The gel was visualized by autoradiography and analyzed with a phosphoimager (Molecular Dynamics). GT purine-pyrimidine mixed DNA oligonucleotides and RNA oligonucleotides were analyzed and compared with a 25-mer pyrimidine sequence in parallel (Seq ID No: 3) and antiparallel (Seq ID No: 42) orientation. To quantitate the effects of the oligonucleotides, the amounts of uncut RNA were determined. The oligonucleotides tested are listed below:

TFO 1 TTTTCTTTTCCCCCCTGACCTTCCC (SEQ ID NO:3) (PY1)

PY2 CCCTTCCAGTCCCCCCTTTTCTTTT (SEQ ID NO:42) (TFO 1)

TFO 1' TTTTGTTTTGGGGGGTGTGGTTGGG (SEQ ID NO:4) (GT1)

GT2 GGGTTGGTGTGGGGGGTTTTGTTTT (SEQ ID NO:39)

GT3 TGGGGGGTTTTGTTTT (SEQ ID NO:40)
TFO 4' TTTTGTTTTGGGGGGT (SEQ ID NO: 6) (GT 4)
GU1 UUUUGUUUUGGGGGGUGUGGUUGGG (SEQ ID NO:41).

As is evident from the above, GU1 was the RNA oligonucleotide tested.

All oligonucleotides tested inhibited RNase H to some degree. The "PY2" pyrimidine sequence (SEQ ID NO:42), the antiparallel of TFO 1, exhibited the lowest degree of inhibition. Oligonucleotide GU1 approached 100% inhibition.

Figure 4:
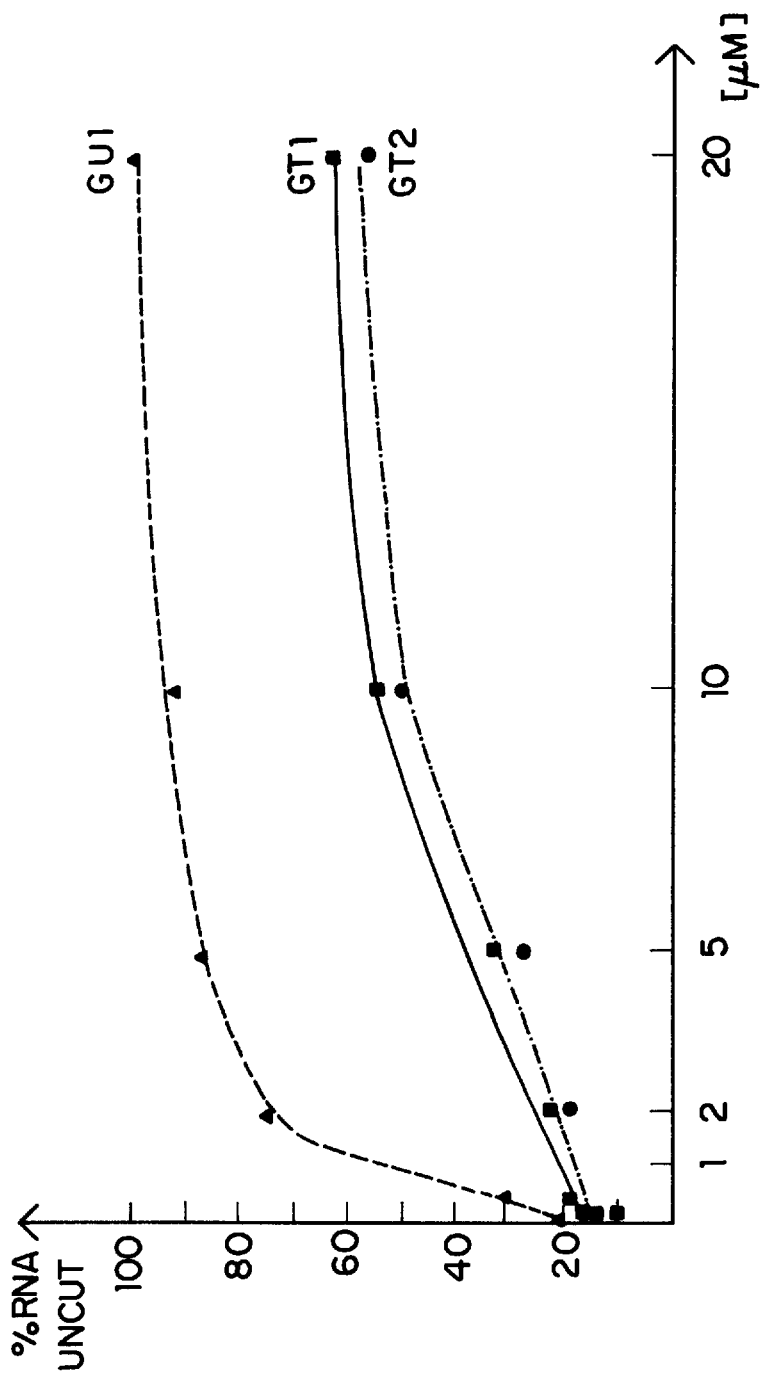
FIG. 4 is a plot of data quantified from a phospho-imager depicting cleavage inhibition by oligonucleotides GT1, GT2, and GU1.

Oligonucleotides GT1, GT2, and GU1 were tested further at a range of concentrations. The concentration ranges are indicated in FIG. 4. The concentrations of the remaining materials were as previously. The quantitative plots of phosphoimager results for GT1, GT2, and GU1 are depicted in FIG. 4. GT1 inhibited the RNase H by 50% at 5.0 $\mu$M, and GU1 inhibited 50% at 0.5 $\mu$M. Since GT1 forms a DNA-RNA-DNA triplex, and GU1 forms a DNA-RNA-RNA triplex, these results indicate that the DNA-RNA-RNA triplex is more protecting.

EXAMPLE 4 SINGLE-STRANDED RNA TRIPLEXES

Chimeric oligonucleotides of the basic formula 5'-A-B-C-3' were tested with single-stranded RNA in a two-strand system. Triplexes were allowed to form in vitro as in Example 3 above, with the exception that the pH was adjusted to 6.5 to comport with what is believed to be the local pH of triplexes which form naturally 4 in vivo. (Personal communication.) Average protection from cleavage was about 50%.

Protection from RNase H was monitored as above. Specifically, protection was monitored in vitro using RNA which was radioactively labeled at its 5'-end. Cleavage was analyzed on a sequencing gel. Cleavage within the PPT region of the RNA leads to a band of about 80 nucleotides. Protection from cleavage results in an uncleavaged full-length RNA. The amount of cleaved versus uncleaved RNA was monitored by phosphoimager.

The oligonucleotide of the formula 5'-A-B-C-3' was synthesized with segment A comprising ribonucleotides and deoxyribonucleotides, alternatively. Segment C was synthesized using deoxyribonucleotides. Ribonucleotides can also be used for segment C. However, if segment A is synthesized using ribonucleotides, it is preferable that segment C be synthesized using deoxyribonucleotides. Greatest protection was achieved with segment A comprising 16 ribonucleotides and segment C comprising 16 deoxyribonucleotides, linked by four thymidines. One hundred percent protection from cleavage was achieved with a phosphorothioate-modified oligonucleotide comprising this structure (SEQ. ID No: 37) at equimolar concentration.

The formation of a triplex at the PPT was confirmed using a primer-extension technique. A primer binding downstream of the PPT RNA was synthesized and extended in vitro by RT in the presence of oligodeoxynucleotides, including one which was radioactively labelled. The newly synthesized DNA was terminated at the site of the PPT when the triplex was formed and blocked extension. Additionally, a melting profile was performed whereby measurements of optical absorption revealing two transition points proved that a triplex had formed.

The chimeric oligonucleotides tested are depicted in Tables 5 through 7. Test designations and triplex conformations are indicated in the first column. Ribonucleotides are indicated in Table 7 with a subscript "r". Also in Table 7, phosphorothioate derivatives of the nucleotides are indicated with a subscript "s". The linker segments are underlined in all tables. All oligonucleotides exhibited formation of a triplex by the test methods used, with the exception of the oligonucleotide labeled TFO A in Table 5 (SEQ. ID No:12).

TFO A is 54-mer which is partially self-complementary and forms a hairpin-type stem-looped structure containing two mismatched regions, a loop and loose ends. See FIGS. 3a and 3b. TFO A completely inhibited cleavage at concentrations less than one nanomolar, in vitro. TFO A takes a structural conformation which resembles that of the PPT and, due to its self-complementarity, is very stable. Thus, it is possible that TFO A's inhibitory effect is strong because it mimics the PPT hybrid region.

TFO A (SEQ ID No:12) was modified through nucleotide changes as reported in Table 6. Through these studies, it was learned that the two bulges are essential for protection of RNA and that the overhanging 5'- and 3'-ends can be shortened. Variances numbered 5037 (SEQ ID NO:26) and 5074 (SEQ ID NO:21) inhibited cleavage to 50% at 50-fold molar excess of the oligonucleotide over the template, i.e., about one $\mu$M oligonucleotide. Ninety-five percent inhibition of the RT occurred at about 25 $\mu$M.

Derivatives of oligonucleotide TFO F tested are presented in Table 7. The phosphorothioate derivative of SEQ ID No:37 ($R_sRD$ in Table 7) resulted in 100% inhibition at the same concentration as the phosphodiester, thereby exhibiting an increase in protection over the phosphodiester form. Derivative TFO $F_1$ (SEQ ID No:38) formed a pseudocircle due to the synthesis of a complementary tail. TFO $F_1$ inhibited RNase H by about 80%. The formation of a pseudocircle may provide increased protection from exonuclease attack.

The foregoing examples are meant to illustrate the invention and not to limit it in any way. Those skilled in the art will recognize that modifications can be made which are within the spirit and scope of the invention as indicated in the appended claims.

TABLE 5
TFO A through F

DESIGNATION

TFO A  5' TTTTCTTTTG GGGGGTTTGG TTGGG<u>TTTTC</u> CCTTCCAGTC CCCCCTTTTC TTTT 3'  (SEQ ID NO:12)

TFO B  5' TGTGTGTGTG TGTGTGTGTG TGTGT<u>TTTT</u> CCCTTCCAGT CCCCCCTTTT CTTTT[1] 3'  (SEQ ID NO:13)

TFO C  5' TTTTATTTTA GGGGATTTGG TTGGG<u>TTTTC</u> CCTTCCAGTC CCCCCTTTTC TTTT 3'  (SEQ ID NO:14)

TABLE 5-continued
TFO A through F

| DESIGNATION | | |
|---|---|---|
| TFO D | 5' TTTTCTTTTG GGGGGTCTGG TTGGG[2] TTTTCCCTTC CAGTCCCCCC TTTTCTTTT 3' | (SEQ ID NO:15) |
| TFO E | 5' TTTTGTTTTG GGGGGT[3] TTTTTCCCCCC TTTTCTTTT 3' | (SEQ ID No:16) |
| TFO F | 5' TTTTCTTTTC CCCCCTTTTT TCCCCCCTTT TCTTTT | (SEQ ID No:17) |

[1] Portion in bold corresponds to SEQ ID No:8.
[2] Portion in bold corresponds to SEQ ID No:4.
[3] Portion in bold corresponds to SEQ ID No:6.

TABLE 6
TFO-A Variants

| DESIGNATION | | | |
|---|---|---|---|
| 4-5-7-2 | 5' | GGG GGG TTT GGT TGG GTT TTC CCA ACC AAA CCC CCC 3' | (SEQ ID NO:18) |
| 4-5-7-1 | 5' | GGG GGG TTT GGT TGG GTT TCC CTT CCA GTC CCC CC 3' | (SEQ ID NO:19) |
| 4-5-7-4 | 5' | GGG GGG TTT GGT TGG GTT TTT TCC CTT CCA GTC CCC 3' | (SEQ ID NO:20) |
| 5-0-7-4 | 5' | AGG GGA TTT GGT TGG GTT TTC CCT TCC AGT CCC CC 3' | (SEQ ID NO:21) |
| 4-5-7-3 | 5' | GGG GGG TTT GGT TGG GTT TTT CCC TTC CAG TCC CCC 3' | (SEQ ID NO:22) |
| 5-1-5-9 | 5' | CCC CCT CTC TTC AAA AGA GAA GGG GGG 3' | (SEQ ID NO:23) |
| 5-1-6-0 | 5' | CCC CCT TCT TCA AAA GAG AGG TTG GGG G 3' | (SEQ ID NO:24) |
| 5-0-7-2 | 5' | GGG GAC TGG GAG GGT TTT CCC TTC CAG TCC CCC 3' | (SEQ ID NO:25) |
| 5-0-3-7 | 5' | TTT TCT TTT GGG GGG TTT GGT TGG GTT TTC CCT TCC AGT CCC CCC TTT TCT TTT 3' (SEQ ID No:26) | |
| RH 1001 | 5' | GGG GGG TTT GGT TGG GTT TTC CCT TCC AGT CCC CCC | (SEQ ID NO:27) |
| RH 1002 | 5' | GGG GGG ACT GGT TGG GTT TTC CCT TCC AGT CCC CCC | (SEQ ID NO:28) |
| RH 1003 | 5' | GGG GGG TTG TCC CCC C 3' | (SEQ ID NO:29) |
| RH 1004 | 5' | GGG GGG TTT GGA AGG GTT TTC CCT TCC AGT CCC CCC | (SEQ ID NO:30) |
| RH 1005 | 5' | GGG GGG ACT GGA AGG GTT TTC CCT TCC AGT CCC CCC | (SEQ ID NO:31) |
| RH 1006 | 5' | TTT GGT TGG GTT TTC CCT TCC AGT 3' | (SEQ ID NO:32) |
| RH 1007 | 5' | GGG GGG NNN GGT TGG GTT TTC CCT TCC AGT CCC CCC | (SEQ ID NO:33) |
| RH 1008 | 5' | GGG GGG TTT GGN NGG GTT TTC CCT TCC AGT CCC CCC | (SEQ ID NO:34) |
| RH 1009 | 5' | GGG GGG TTT GGT TGN NTT TTC CCT TCC AG CCC CCC 3' | (SEQ ID NO:35) |
| RH 1010 | 5' | GGG GGG TTT GGT TGG GTT TTC CCT TCC AGT CCC CCC TTT TCT TTT 3' (SEQ ID NO:36) | |

TABLE 7

TFO-F Derivatives

| DESIGNATION/<br>TRIPLEX | |
|---|---|
| TFO F/DRD | 5' TTT TCT TTT CCC CCC <u>TTT TTT</u> CCC CCC TTT TCT TTT 3' (SEQ ID NO:17) |
| DR1/RRD | 5' UUU UC$_r$U UUU C$_r$C$_r$C$_r$ C$_r$C$_r$C$_r$ U<u>TT TT</u> TCC CCC CTT TTC TTT T 3' (SEQ ID NO:37) |
| DR2/RsRD | 5' U$_s$U$_s$U$_s$ U$_s$C$_s$U$_s$ U$_s$U$_s$U$_s$ C$_s$C$_s$C$_s$ C$_s$C$_s$C$_s$ U$_s$<u>TT TT</u> TCC CCC CTT TTC TTT T 3' (SEQ ID NO:37) |
| Thio/DsRD | 5' T$_s$T$_s$T$_s$ T$_s$C$_s$T$_s$ T$_s$T$_s$T$_s$ C$_s$C$_s$C$_s$ C$_s$C$_s$C$_s$ <u>TTT TTT</u> CCC CCC TTT TCT TTT 3' (SEQ ID NO:17) |
| TFO F$_1$<br>(pseudo-<br>circle) | 5' GCA TGC CCT TTT CTT TTC CCC CCT <u>TTT TTC</u> CCC CCT TTT CTT TTC C<br>    GCA TGC 3' (SEQ ID NO:38) |

---

What is claimed is:

1. An oligonucleotide of from about 25 to about 54 nucleotides comprising UUUUGUUUUGGGGGUGUGGUUGGG (SEQ ID NO:41) which binds to a polypurine-rich tract of an RNA-DNA hybrid containing pyrimidines within a sequence of contiguous purines of a viral nucleic acid having said tract, or a derivative of said oligonucleotide for enhancing stability to nuclease attack and/or increasing cellular uptake.

2. An oligonucleotide of from about 25 to about 54 nucleotides comprising TTTTCTTTTCCCCCCTGACCTTCCC (SEQ ID NO:3) which binds to a polypurine-rich tract of an RNA-DNA hybrid containing pyrimidines within a sequence of contiguous purines of a viral nucleic acid having said tract, or a derivative of said oligonucleotide for enhancing stability to nuclease attack and/or increasing cellular uptake.

3. An oligonucleotide of from about 25 to about 54 nucleotides comprising AAAAGAAAAGGGGGACTGGAGGG (SEQ ID NO:7) which binds to a polypurine-rich tract of an RNA-DNA hybrid containing pyrimidines within a sequence of contiguous purines of a viral nucleic acid having said tract, or a derivative of said oligonucleotide for enhancing stability to nuclease attack and/or increasing cellular uptake.

4. An oligonucleotide of from about 25 to about 54 nucleotides comprising CCCTTCCAGTCCCCCTTTTCTTTT (SEQ ID NO:8) which binds to a polypurine-rich tract of an RNA-DNA hybrid containing pyrimidines within a sequence of contiguous purines of a viral nucleic acid having said tract, or a derivative of said oligonucleotide for enhancing stability to nuclease attack and/or increasing cellular uptake.

5. An oligonucleotide of about 54 nucleotides comprising TTTTCTTTTGGGGGTTTGGTTGGGTTTTCCCTTCCAGTCCCCCTTTTCTTTT (SEQ ID NO:12) which binds to a polypurine-rich tract containing pyrimidines within a sequence of contiguous purines of a viral nucleic acid having said tract, or a derivative of said oligonucleotide for enhancing stability to nuclease attack and/or increasing cellular uptake.

* * * * *

UNITED STATES PATENT AND TRADEMARK OFFICE
CERTIFICATE OF CORRECTION

PATENT NO. : 5,849,900
DATED : December 15, 1998
INVENTOR(S) : Karin Moelling

It is certified that error appears in the above-identified patent and that said Letters Patent is hereby corrected as shown below:

Col. 10, line 23, replace "Best" with -- West --.

Col. 10, line 29, replace "[$\gamma$-$^{32}$P]UTP" with -- [$\alpha$-$^{32}$P]UTP --.

Col. 11, line 16, replace "TEE-urea-polyacrylamide" with -- TBE-urea-polyacrylamide --.

Col. 11, line 28, replace "TEE-urea" with -- TBE-urea --.

Col. 11, line 40, replace "TEE-urea-polyacrylamide" with -- TBE-urea-polyacrylamide --.

Col. 14, line 51, replace "polyacrylamide-TEE-urea" with -- polyacrylamide-TBE-urea --.

Signed and Sealed this

Eighth Day of June, 1999

*Attest:*

Q. TODD DICKINSON

*Attesting Officer*   Acting Commissioner of Patents and Trademarks

SEQUENCE LISTING ( 1 ) GENERAL INFORMATION:

( i i i ) NUMBER OF SEQUENCES: 42

( 2 ) INFORMATION FOR SEQ ID NO: 1:

( i ) SEQUENCE CHARACTERISTICS:
        ( A ) LENGTH: 16
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 1:

A A A A G A A A A G  G G G G G A                           1 6

( 2 ) INFORMATION FOR SEQ ID NO: 2:

( i ) SEQUENCE CHARACTERISTICS:
        ( A ) LENGTH: 26
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 2:

A A A A G A A A A G  G G G G G A C T G G  A A G G G C           2 6

( 2 ) INFORMATION FOR SEQ ID NO: 3:

( i ) SEQUENCE CHARACTERISTICS:
        ( A ) LENGTH: 25
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 3:

T T T T C T T T T C  C C C C C T G A C C  T T C C C             2 5

( 2 ) INFORMATION FOR SEQ ID NO: 4:

( i ) SEQUENCE CHARACTERISTICS:
        ( A ) LENGTH: 25
        ( B ) TYPE: Nucleic Acid
        ( C ) STRANDEDNESS: Single (D) TOPOLOGY: Linear (iv) ANTI-SENSE: Yes (xi) SEQUENCE DESCRIPTION: SEQ ID NO: 4:

TTTTGTTTTG GGGGGTGTGG TTGGG 25

(2) INFORMATION FOR SEQ ID NO: 5:

(i) SEQUENCE CHARACTERISTICS:
(A) LENGTH: 16
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 5:

TTTTCTTTTC CCCCCT 16

(2) INFORMATION FOR SEQ ID NO: 6:

(i) SEQUENCE CHARACTERISTICS:
(A) LENGTH: 16
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 6:

TTTTGTTTTG GGGGGT 16

(2) INFORMATION FOR SEQ ID NO: 7:

(i) SEQUENCE CHARACTERISTICS:
(A) LENGTH: 25
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 7:

AAAAGAAAAG GGGGGACTGG AAGGG 25

(2) INFORMATION FOR SEQ ID NO: 8:

(i) SEQUENCE CHARACTERISTICS:
(A) LENGTH: 25
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 8:

CCCTTCCAGT CCCCCTTTT CTTTT 25

(2) INFORMATION FOR SEQ ID NO: 9:

(i) SEQUENCE CHARACTERISTICS:
(A) LENGTH: 40
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 9:

TGAATTAGCC CTTCCAGTCC CCCCTTTTCT TTTAAAAAGT 40

( 2 ) INFORMATION FOR SEQ ID NO: 10:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 10:

AGTCCCCCCT TTTCTTTTAA 20

( 2 ) INFORMATION FOR SEQ ID NO: 11:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 11:

CCGCCCAGGC CACGCCTCCC 20

( 2 ) INFORMATION FOR SEQ ID NO: 12:

( i ) SEQUENCE CHARACTERISTICS:
        ( A ) LENGTH: 54
        ( B ) TYPE: Nucleic Acid
        ( C ) STRANDEDNESS: Single
        ( D ) TOPOLOGY: Unknown ( i v ) ANTI-SENSE: Yes ( x i ) SEQUENCE DESCRIPTION: SEQ ID NO: 12:

TTTCTTTTG GGGGGTTTGG TTGGGTTTTC CCTTCCAGTC CCCCCTTTTC 50

TTTT 54

( 2 ) INFORMATION FOR SEQ ID NO: 13:

( i ) SEQUENCE CHARACTERISTICS:
        ( A ) LENGTH: 54
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 13:

TGTGTGTGTG TGTGTGTGTG TGTGTTTTTC CCTTCCAGTC CCCCCTTTTC 50

TTTT 54

( 2 ) INFORMATION FOR SEQ ID NO: 14:

( i ) SEQUENCE CHARACTERISTICS:
        ( A ) LENGTH: 54
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 14:

TTTTATTTTA GGGGATTTGG TTGGGTTTTC CCTTCCAGTC CCCCCTTTTC 50

TTTT 54

(2) INFORMATION FOR SEQ ID NO: 15:

(i) SEQUENCE CHARACTERISTICS:
        (A) LENGTH: 54
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 15:

TTTCTTTTG GGGGTCTGG TTGGGTTTTC CCTTCCAGTC CCCCCTTTTC 50

TTTT 54

(2) INFORMATION FOR SEQ ID NO: 16:

(i) SEQUENCE CHARACTERISTICS:
        (A) LENGTH: 36
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 16:

TTTTGTTTTG GGGGTTTTT TCCCCCCTTT TCTTTT 36

(2) INFORMATION FOR SEQ ID NO: 17:

(i) SEQUENCE CHARACTERISTICS:
        (A) LENGTH: 36
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 17:

TTTTCTTTTC CCCCTTTTT TCCCCCCTTT TCTTTT 36

(2) INFORMATION FOR SEQ ID NO: 18:

(i) SEQUENCE CHARACTERISTICS:
        (A) LENGTH: 36
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 18:

GGGGGGTTTG GTTGGGTTTT CCCAACCAAA CCCCCC 36

(2) INFORMATION FOR SEQ ID NO: 19:

(i) SEQUENCE CHARACTERISTICS:
        (A) LENGTH: 35
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 19:

GGGGGGTTTG GTTGGGTTTC CCTTCCAGTC CCCCC 35

( 2 ) INFORMATION FOR SEQ ID NO: 20:

( i ) SEQUENCE CHARACTERISTICS:
        ( A ) LENGTH: 36
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 20:

GGGGGGTTTG GTTGGGTTTT TTCCCTTCCA GTCCCC　　　　　　　　　　　　36

( 2 ) INFORMATION FOR SEQ ID NO: 21:

( i ) SEQUENCE CHARACTERISTICS:
        ( A ) LENGTH: 35
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 21:

AGGGGATTTG GTTGGGTTTT CCCTTCCAGT CCCCC　　　　　　　　　　　　35

( 2 ) INFORMATION FOR SEQ ID NO: 22:

( i ) SEQUENCE CHARACTERISTICS:
        ( A ) LENGTH: 35
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 22:

GGGGGGTTTG GTTGGGTTTT CCCTTCCAGT CCCCC　　　　　　　　　　　　35

( 2 ) INFORMATION FOR SEQ ID NO: 23:

( i ) SEQUENCE CHARACTERISTICS:
        ( A ) LENGTH: 27
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 23:

CCCCCTCTCT TCAAAAGAGA AGGGGGG　　　　　　　　　　　　　　　　27

( 2 ) INFORMATION FOR SEQ ID NO: 24:

( i ) SEQUENCE CHARACTERISTICS:
        ( A ) LENGTH: 28
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 24:

CCCCCTTCTT CAAAGAGAG GTTGGGGG　　　　　　　　　　　　　　　28

( 2 ) INFORMATION FOR SEQ ID NO: 25:

( i ) SEQUENCE CHARACTERISTICS:

(A) LENGTH: 33
                (B) TYPE: Nucleic Acid
                (C) STRANDEDNESS: Single
                (D) TOPOLOGY: Linear (iv) ANTI-SENSE: Yes (xi) SEQUENCE DESCRIPTION: SEQ ID NO: 25:

GGGGACTGGG AGGGTTTTCC CTTCCAGTCC CCC 33

(2) INFORMATION FOR SEQ ID NO: 26:

(i) SEQUENCE CHARACTERISTICS:
                (A) LENGTH: 54
                (B) TYPE: Nucleic Acid
                (C) STRANDEDNESS: Single
                (D) TOPOLOGY: Linear (iv) ANTI-SENSE: Yes (xi) SEQUENCE DESCRIPTION: SEQ ID NO: 26:

TTTCTTTTG GGGGTTTGG TTGGGTTTTC CCTTCCAGTC CCCCCTTTTC 50

TTTT 54

(2) INFORMATION FOR SEQ ID NO: 27:

(i) SEQUENCE CHARACTERISTICS:
                (A) LENGTH: 36
                (B) TYPE: Nucleic Acid
                (C) STRANDEDNESS: Single
                (D) TOPOLOGY: Linear (iv) ANTI-SENSE: Yes (xi) SEQUENCE DESCRIPTION: SEQ ID NO: 27:

GGGGGGTTTG GTTGGGTTTT CCCTTCCAGT CCCCCC 36

(2) INFORMATION FOR SEQ ID NO: 28:

(i) SEQUENCE CHARACTERISTICS:
                (A) LENGTH: 36
                (B) TYPE: Nucleic Acid
                (C) STRANDEDNESS: Single
                (D) TOPOLOGY: Linear (iv) ANTI-SENSE: Yes (xi) SEQUENCE DESCRIPTION: SEQ ID NO: 28:

GGGGGGACTG GTTGGGTTTT CCCTTCCAGT CCCCCC 36

(2) INFORMATION FOR SEQ ID NO: 29:

(i) SEQUENCE CHARACTERISTICS:
                (A) LENGTH: 16
                (B) TYPE: Nucleic Acid
                (C) STRANDEDNESS: Single
                (D) TOPOLOGY: Linear (iv) ANTI-SENSE: Yes (xi) SEQUENCE DESCRIPTION: SEQ ID NO: 29:

GGGGGGTTGT CCCCCC 16

(2) INFORMATION FOR SEQ ID NO: 30:

(i) SEQUENCE CHARACTERISTICS:
                (A) LENGTH: 36
                (B) TYPE: Nucleic Acid
                (C) STRANDEDNESS: Single (D) TOPOLOGY: Linear (iv) ANTI-SENSE: Yes (xi) SEQUENCE DESCRIPTION: SEQ ID NO: 30:

GGGGGGTTTG GAAGGGTTTT CCCTTCCAGT CCCCCC                              36

(2) INFORMATION FOR SEQ ID NO: 31:

(i) SEQUENCE CHARACTERISTICS:
        (A) LENGTH: 36
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 31:

GGGGGGACTG GAAGGGTTTT CCCTTCCAGT CCCCCC                              36

(2) INFORMATION FOR SEQ ID NO: 32:

(i) SEQUENCE CHARACTERISTICS:
        (A) LENGTH: 24
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 32:

TTTGGTTGGG TTTTCCCTTC CAGT                                           24

(2) INFORMATION FOR SEQ ID NO: 33:

(i) SEQUENCE CHARACTERISTICS:
        (A) LENGTH: 36
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 33:

GGGGGGNNNG GTTGGGTTTT CCCTTCCAGT CCCCCC                              36

(2) INFORMATION FOR SEQ ID NO: 34:

(i) SEQUENCE CHARACTERISTICS:
        (A) LENGTH: 36
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 34:

GGGGGGTTTG GNNGGGTTTT CCCTTCCAGT CCCCCC                              36

(2) INFORMATION FOR SEQ ID NO: 35:

(i) SEQUENCE CHARACTERISTICS:
        (A) LENGTH: 35
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 35:

GGGGGGTTTG GTTGNNTTTT CCCTTCCAGC CCCCC 35

(2) INFORMATION FOR SEQ ID NO: 36:

(i) SEQUENCE CHARACTERISTICS:
        (A) LENGTH: 45
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 36:

GGGGGGTTTG GTTGGGTTTT CCCTTCCAGT CCCCCTTTT CTTTT 45

(2) INFORMATION FOR SEQ ID NO: 37:

(i) SEQUENCE CHARACTERISTICS:
        (A) LENGTH: 36
        (B) TYPE: Nucleic Acid
        (C) STRANDEDNESS: Single
        (D) TOPOLOGY: Unknown (iv) ANTI-SENSE: Yes (xi) SEQUENCE DESCRIPTION: SEQ ID NO: 37:

UUUUCUUUUC CCCCCUTTTT TCCCCCCTTT TCTTTT 36

(2) INFORMATION FOR SEQ ID NO: 38:

(i) SEQUENCE CHARACTERISTICS:
        (A) LENGTH: 52
        (B) TYPE: Nucleic Acid
        (C) STRANDEDNESS: Single
        (D) TOPOLOGY: Unknown (iv) ANTI-SENSE: Yes (xi) SEQUENCE DESCRIPTION: SEQ ID NO: 38:

GCATGCCCTT TTCTTTTCCC CCCTTTTTTC CCCCCTTTTC TTTTCCGCAT GC 52

(2) INFORMATION FOR SEQ ID NO: 39:

(i) SEQUENCE CHARACTERISTICS:
        (A) LENGTH: 25
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 39:

GGGTTGGTGT GGGGGGTTTT GTTTT 25

(2) INFORMATION FOR SEQ ID NO: 40:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 40:

TGGGGGGTTT TGTTTT 16

(2) INFORMATION FOR SEQ ID NO: 41:

(  i  ) SEQUENCE CHARACTERISTICS:
    ( A ) LENGTH: 25
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 41:

UUUUGUUUUG GGGGGUGUGG UUGGG    25

( 2 ) INFORMATION FOR SEQ ID NO: 42:

(  i  ) SEQUENCE CHARACTERISTICS:
    ( A ) LENGTH: 25
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 42:

CCCTTCCAGT CCCCCTTTT CTTTT    25